United States Patent [19]

Rohde et al.

[11] Patent Number: 5,641,871
[45] Date of Patent: Jun. 24, 1997

[54] PREPARATION OF METALLOCENES IN ONE REACTION STEP

[75] Inventors: Wolfgang Rohde, Speyer; Hans-Helmut Görtz, Freinsheim; Udo Handrich, Hassloch, all of Germany

[73] Assignee: BASF Aktiengesellschaft

[21] Appl. No.: 328,776

[22] Filed: Oct. 28, 1994

[30] Foreign Application Priority Data

Oct. 30, 1993 [DE] Germany ............... 43 37 230.9

[51] Int. Cl.$^6$ ............... C07F 5/00; C07F 17/00; C07F 7/00; C07F 11/00
[52] U.S. Cl. ............... 534/15; 556/43; 556/46; 556/53; 556/58; 556/136; 556/144
[58] Field of Search ............... 556/53, 58, 43, 556/46, 136, 144; 534/15

[56] References Cited

U.S. PATENT DOCUMENTS 2,834,796  5/1958  Barusch et al. ............... 260/439
2,870,183  1/1959  Brantley ............... 260/438

FOREIGN PATENT DOCUMENTS 1416543  12/1975  United Kingdom .

OTHER PUBLICATIONS

*Chem. Abst.*, vol. 91, No. 21, Nov. 19, 1979, abst. No. 175478t, Handlir et al., "A simple synthetic method for chromocene and vanadocene", p. 678.

*Primary Examiner*—Porfirio Nazario-Gonzales
*Attorney, Agent, or Firm*—Keil & Weinkauf

[57] ABSTRACT

Metallocenes are prepared by a process in which a metal salt is reacted with at least one alkali metal and with an unsaturated, cyclic hydrocarbon in the presence of a solvent in one reaction step.

6 Claims, No Drawings

PREPARATION OF METALLOCENES IN ONE REACTION STEP

The present invention relates to processes for the preparation of metallocenes.

Metallocenes are usually prepared by reacting a metal salt with a cyclopentadienyl-alkali metal or cyclopentadienyl-alkaline earth metal compound in an inert solvent. For metallocene preparation on an industrial scale, this means that the desired cyclopentadienyl-alkali metal or cyclopentadienyl-alkaline earth metal compound is prepared separately in a first reactor or reaction step and is then reacted with the metal salt in a second reactor or reaction step. Processes of this type are described in U.S. Pat. No. 2,870,183 and GB-A 1 416 543.

These known processes have the disadvantage that high capital costs are required for a plant having two separate reaction containers. If the metallocenes are prepared in two reaction steps in one reactor, the utilization of the reactor for the actual metallocene preparation is low and in addition dead times are required for cleaning between the particular reaction steps and sufficient container capacity must be available for intermediate storage of at least one of the reactants.

It is an object of the present invention to remedy the disadvantages described and to provide a technically simpler and more economical process for the preparation of metallocenes.

We have found that this object is achieved by a process for the preparation of metallocenes in which a metal salt is reacted with at least one alkali metal and with unsaturated, cyclic hydrocarbons in the presence of a solvent in one reaction step.

The novel process is particularly suitable for the preparation of metallocenes of the formula I

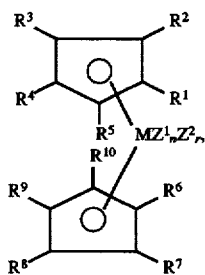

where $R^1$ to $R^{10}$ are each hydrogen, $C_1$–$C_{10}$-alkyl, 5-membered to 7-membered cycloalkyl which in turn may carry $C_1$–$C_6$-alkyl groups as substituents, $C_6$–$C_{15}$-aryl or arylalkyl, where two adjacent radicals together may furthermore be a cyclic group of 4 to 15 carbon atoms, or $Si(R^{11})_3$, $R^{11}$ is $C_1$–$C_{10}$-alkyl, $C_6$–$C_{15}$-aryl or $C_3$–$C_{10}$-cycloalkyl, or $R^4$ and $R^9$ together form a group —$[Y(R^{12}R^{13})]_m$—, Y is silicon, germanium, tin or carbon, $R^{12}$ and $R^{13}$ are each hydrogen, $C_1$–$C_{10}$-alkyl, $C_3$–$C_{10}$-cycloalkyl or $C_6$–$C_{15}$-aryl, m is 1, 2, 3 or 4, M is a metal of subgroups IV to VIII or a metal of the lanthanide series, $Z^1$ and $Z^2$ are each fluorine, chlorine, bromine, iodine, —$OR^{14}$, —$OOCR^{14}$,

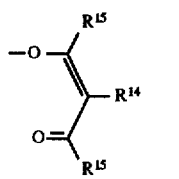

or

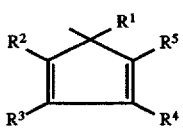

or

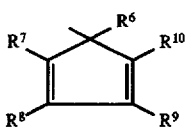

where $R^{14}$ is hydrogen or $C_1$–$C_{20}$-alkyl, $R^{15}$ is $C_1$–$C_{20}$-alkyl and n and r are each 0, 1 or 2, the sum n+r likewise being 0, 1 or 2.

The term metallocenes is therefore understood as meaning those compounds in which a transition metal atom is bonded via π bonds to unsaturated cyclic carbon radicals, for example cyclopentadienyl, fluorenyl or indenyl.

Preferred metallocenes of the general formula I are those in which $R^1$ to $R^{10}$ are each hydrogen or $C_1$–$C_6$-alkyl or two adjacent radicals together form a cyclic group of 4 to 15, preferably 8 to 15, carbon atoms, M is titanitun, zirconium, hafnium, vanadium, niobium, tantalum, chromium, molybdenum, tungsten, manganese, iron, ruthenium, osmium, cobalt or nickel, in particular titanium, zirconium, hafnium, chromium or iron, and $Z^1$ and $Z^2$ are each chlorine.

Other preferred metallocenes of the general formula I are those in which the unsaturated cyclic hydrocarbon radicals

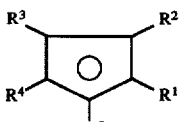

and

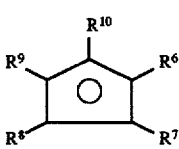

are identical.

Examples of particularly preferred metallocenes of the general formula I are bis(cyclopentadienyl)chromium, bis(cyclopentadienyl)dichlorotitanimm, bis(cyclopentadienyl)dichlorozirconium, bis(cyclopentadienyl)dichlorohafnium and bis(cyclopentadienyl)iron.

In the novel process, metal salts of the formula II $MX_rL_q$      II are preferably used.

Regarding the meaning and preferred meaning of M, reference may be made to the statements made in the case of the metallocenes of the formula I. X is fluorine, chlorine, bromine, iodine, —OR$^{14}$, —OOCR$^{14}$ or

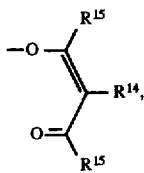

where R$^{14}$ is hydrogen or C$_1$–C$_{20}$-alkyl, preferably C$_1$–C$_8$-alkyl and R$^{15}$ is C$_1$–C$_{20}$-alkyl, preferably C$_1$–C$_8$-alkyl. X is preferably chlorine. In the case of a plurality of substituents X, they may also have different meanings. L is a neutral ligand, for example a tertiary amine, such as trimethylamine or triethylamine, a polynuclear tertiary amine, such as N,N'-tetramethylethylenediamine, or an aromatic tertiary amine, for example pyridine. L may furthermore be an aliphatic open-chain or cyclic, monofunctional or polyfunctional ether, for example diethyl ether, tetrahydrofuran or 1,2-dimethoxyethane.

p depends on the valency of the metal M and is 2, 3, 4, 5 or 6. q is 0, 1, 2, 3 or 4, preferably 0 or 1.

Preferred metal salts of the formula II are CrCl$_2$, CrCl$_3$, TiCl$_4$, ZrCl$_4$, HfCl$_4$ and FeCl$_2$.

In the novel process, lithium, sodium or potassium is preferably used as the alkali metal. Alloys of a plurality of alkali metals may also be used. The alkali metal is preferably used in finely divided form. The molar ratio of alkali metal to metal salt is preferably from 2:1 to 20:1, in particular from 2:1 to 10:1.

In the novel process,

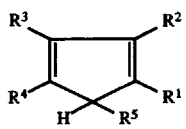

and

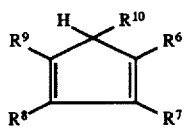

are preferably used as unsaturated, cyclic hydrocarbons; with regard to the meanings of R$^1$ to R$^{10}$ and their preferred meanings, reference may be made to the statements made in the case of metallocenes of the general formula I.

Where R$^4$ and R$^9$ together form a group —[Y(R$^{12}$R$^{13}$)]$_m$—, the bridged compounds are used as unsaturated, cyclic hydrocarbons.

Hence, the following unsaturated, cyclic hydrocarbons are particularly used:
cyclopentadiene, indene and fluorene.

The molar ratio of unsaturated, cyclic hydrocarbons to alkali metals is preferably from 1:1 to 10:1, in particular from. 1:1 to 5:1. The molar amount of unsaturated, cyclic hydrocarbons is understood here as meaning the total molar amount of unsaturated, cyclic hydrocarbons if different hydrocarbons of this type are used. If the unsaturated, cyclic hydrocarbons used are those which have a group —[Y(R$^{12}$R$^{13}$)]$_m$—, both unsaturated cyclic systems are taken into account when calculating the molar amount. If the unsaturated, cyclic hydrocarbons are used in molar excess, based on the amount of alkali metals, these unsaturated, cyclic hydrocarbons may also account for the substituents Z$^1$ and/or Z$^2$.

Suitable solvents in the novel process are those which do not react with the reactants used but in which the metal salts are partially or completely soluble. Solvents of this type which may be used are aliphatic and aromatic hydrocarbons, for example heptane or toluene, and open-chain and cyclic ethers, for example diethyl ether or tetrahydrofuran. Mixtures of different solvents may also be used. Open-chain and cyclic ethers are preferred.

The amount of solvent is in principle not critical, but from 10 to 100 ml, based on 1 g of metal salt, are preferably used.

The novel process can be carried out at from −100 to +200, preferably from −80 to +100, in particular from +10° to +70, °C., and from 0.1 to 100, preferably from 0.5 to 2, bar. The reaction times are in general from 0.1 to 20, preferably from 0.5 to 2, hours.

The novel process is preferably carried out by adding the solvent to the metal salt in a stirred kettle operated by a batchwise method, adding the alkali metal to the mixture and then adding the unsaturated, cyclic hydrocarbons, preferably with stirring.

The reaction thus takes place in one reaction step and in one reactor, ie. in one reaction zone.

The metallocenes prepared by the novel process can be isolated in pure form by the conventional methods, such as crystallization, extraction, sublimation or chromatography. They are suitable, for example, as catalysts, for example for the polymerization of olefins, as stabilizers, as plastics additives and fuel additives and as sunscreen agents.

The novel process for the preparation of metallocenes is distinguished by uncomplicated process engineering and high cost-efficiency.

EXAMPLES

Example A

Preparation of chromium(II) chloride 1 ml of acetyl chloride and 0.4 ml of methanol were added to a suspension of 30.9 g (≘0.20 mol) of anhydrous chromium(III) chloride and 15.2 g (≘0.29 mol) of chromium powder in 450 ml of anhydrous tetrahydrofuran (THF) under an argon atmosphere for depassivating the metallic chromium. The mixture was refluxed for 7 hours until the violet chromium(III) chloride had been completely converted into the white chromium(II) chloride. Excess hydrogen chloride was then removed in the course of 30 minutes by passing in argon.

EXAMPLES 1 AND 2

Preparation of bis(cyclopentadienyl)chromium (chromocene) in one reaction step

Example 1

In a reactor operated batchwise, 16.8 g (≘0.73 mol) of sodium in the form of cubes having an edge length of about 5 mm were added at room temperature to 36.9 g (≘0.3 mol) of the chromium(II) chloride prepared according to Example A, in THF. 60.4 g (≘0.91 mol) of freshly distilled cyclopentadiene were added in the course of 5 minutes while stirring at 30° C. The reaction temperature was kept at 30° C. by cooling. After the end of the reaction, refluxing was continued for a further hour. The solvent was then removed at room temperature under reduced pressure. The resulting chromocene was isolated from the dry residue by sublimation (greatly reduced pressure; from 100° to 150° C.).

Yield: 30.7 g (56.3% of theory) Melting point: 173° C. Composition: Calculated: 65.96% C 5.49% H 28.55% Cr Found: 65.9% C 5.6% H 28.5% Cr

Example 2

In a reactor operated batchwise, 16.8 g of sodium in the form of cubes having an edge length of about 5 mm were added at room temperature to 36.9 g of the chromium(II) chloride prepared according to Example A, in THF, these tests being carried out similarly to Example 1. However, 96.8 g (=1.46 mol) of freshly distilled cyclopentadiene were added in the course of 2 minutes while stirring at 30° C. During this procedure, the reaction mixture warmed up to 62° C. (boiling point of the THF) in the course of 5 minutes. After 15 minutes, the reaction had ceased and the reaction mixture was refluxed for a further hour by heating. The solvent was then removed at room temperature under reduced pressure. The resulting chromocene was isolated from the dry residue by sublimation.

Yield: 38.8 g (71% of theory) Melting point: 173° C. Composition: Found: 65.7% C 5.5% H 28.1% Cr

COMPARATIVE EXAMPLE VI

Preparation of chromocene in two reaction steps

In a reactor I, 35.6 g (=0.29 mol) of chromium(II) chloride in THF were prepared from a suspension of 30.1 g (=0.19 mol) of anhydrous chromium(III) chloride and 14.8 g (=0.28 mol) of chromium powder in 400 ml of anhydrous THF, this step being carried out similarly to Example A. At the same time, 52.8 g (=0.6 mol) of cyclopentadienylsodium were prepared in a reactor II from 13.8 g (=0.60 mol) of sodium in the form of cubes having an edge length of about 5 mm in 200 ml of anhydrous THF and 59.5 g (=0.90 mol) of freshly distilled cyclopentadiene. The resulting solution of cyclopentadienylsodium in THF was added in the course of 3 minutes to the chromium(II) chloride in THF in reactor I. The reaction mixture was then refluxed for 1 hour. The solvent was then removed at room temperature under reduced pressure. The resulting chromocene was isolated from the dry residue by sublimation.

Yield: 46.1 g (87.3% of theory) Melting point: 173° C. Composition: 65.4% C 5.5% H 28.3% Cr In all Examples and Comparative Examples, C, H and Cr were separately determined in the elemental analysis. If the sum of percentages found differs from 100%, this is due to the usual measurement errors.

We claim:

1. A process for the preparation of a metallocene which comprises: reacting a metal salt with at least one alkali metal and with an unsaturated, cyclic hydrocarbon in the presence of a solvent to form the metallocene from these components in a sinqle reaction step.

2. A process as defined in claim 1, wherein the molar ratio of alkali metal to metal salt is from 2:1 to 20:1.

3. A process as defined in claim 1, wherein the molar ratio of unsaturated, cyclic hydrocarbon to alkali metal is from 1:1 to 10:1.

4. A process as defined in claim 1, wherein the preparation of the metallocene is carried out at from −100° to +200° C. and from 0.1 to 100 bar.

5. A process as defined in claim 1, wherein the metal salt is a compound of the formula II $$MX_pL_q \qquad II,$$

where

M is a metal of subgroups IV to VIII or a metal of the lanthanide series,

X is fluorine, chlorine, bromine, iodine, —OR$^{14}$, —OOCR$^{14}$ or

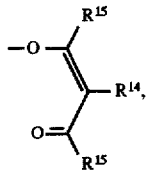

where

R$^{14}$ is hydrogen or C$_1$–C$_{20}$-alkyl,

R$^{15}$ is C$_1$–C$_{20}$-alkyl,

L is a tertiary amine or an ether, p is 2, 3, 4, 5 or 6 and q is 0, 1, 2, 3 or 4.

6. A process as defined in claim 1, wherein the metallocene is of the formula I

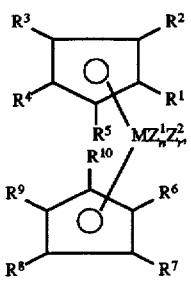

where

R$^1$ to R$^{10}$ are each hydrogen, C$_1$–C$_{10}$-alkyl, 5-membered to 7-membered cycloalkyl which in turn may carry C$_1$–C$_6$-alkyl groups as substituents, C$_6$–C$_{15}$-aryl or arylalkyl, where two adjacent radicals together may furthermore be a cyclic group of 4 to 15 carbon atoms, or Si(R$^{11}$)$_3$, R$^{11}$ is C$_1$–C$_{10}$-alkyl, C$_6$–C$_{15}$-aryl or C$_3$–C$_{10}$-cycloalkyl, or R$^4$ and R$^9$ together form a group —[Y(R$^{12}$R$^{13}$)]$_m$—, Y is silicon, germanium, tin or carbon, R$^{12}$ and R$^{13}$ are each hydrogen, C$_1$–C$_{10}$-alkyl, C$_3$–C$_{10}$-cycloalkyl or C$_6$–C$_{15}$-aryl, m is 1, 2, 3 or 4, M is a metal of subgroups IV to VIII or a metal of the lanthanide series, Z$^1$ and Z$^2$ are each fluorine, chlorine, bromine, iodine, —OR$^{14}$, —OOCR$^{14}$,

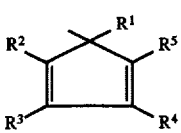

or

-continued
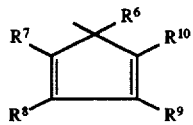
$R^{14}$ is hydrogen or $C_1$–$C_{20}$-alkyl,
$R^{15}$ is $C_1$–$C_{20}$-alkyl and
n and r are each 0, 1 or 2,
the sum n+r likewise being 0, 1 or 2.
* * * * *

UNITED STATES PATENT AND TRADEMARK OFFICE
CERTIFICATE OF CORRECTION

PATENT NO.: 5,641,871

DATED: June 24, 1997

INVENTOR(S): ROHDE et al.

It is certified that error appears in the above-identified patent and that said Letters Patent is hereby corrected as shown below:

Column 5, claim 1, line 55, "sinqle" should be --single--.

Column 6, claim 6, formula I at lines 27-38, delete the present formula and substitute the following:

-- 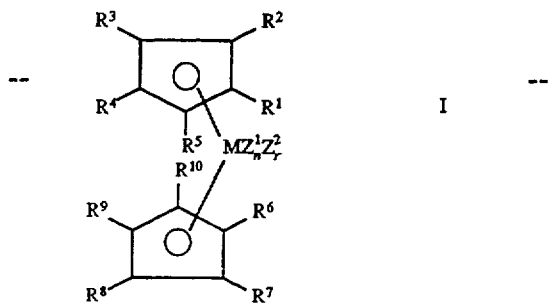 I --

Signed and Sealed this

Nineteenth Day of August, 1997

*Attest:*

BRUCE LEHMAN

*Attesting Officer*           *Commissioner of Patents and Trademarks*